(12) United States Patent
Kawaguchi et al.

(10) Patent No.: US 10,035,781 B2
(45) Date of Patent: Jul. 31, 2018

(54) PROCESS FOR PRODUCING ETHYLENE OXIDE

(71) Applicant: NIPPON SHOKUBAI CO., LTD., Osaka (JP)

(72) Inventors: Yukimasa Kawaguchi, Osaka (JP); Hideto Suzuki, Osaka (JP)

(73) Assignee: NIPPON SHOKUBAI CO., LTD, Osaka (JP)

( * ) Notice: Subject to any disclaimer, the term of this patent is extended or adjusted under 35 U.S.C. 154(b) by 0 days.

(21) Appl. No.: 15/300,637

(22) PCT Filed: Mar. 31, 2015

(86) PCT No.: PCT/JP2015/060265
§ 371 (c)(1),
(2) Date: Sep. 29, 2016

(87) PCT Pub. No.: WO2015/152298
PCT Pub. Date: Oct. 8, 2015

(65) Prior Publication Data
US 2017/0107188 A1  Apr. 20, 2017

(30) Foreign Application Priority Data

Mar. 31, 2014  (JP) .................................. 2014-074438

(51) Int. Cl.
*C07D 301/10*  (2006.01)
(52) U.S. Cl.
CPC .................................. *C07D 301/10* (2013.01)
(58) Field of Classification Search
CPC .................................................. C07D 301/10
See application file for complete search history.

(56) References Cited

U.S. PATENT DOCUMENTS

| | | | |
|---|---|---|---|
| 4,778,567 A | 10/1988 | Kakimoto et al. | |
| 5,262,551 A | 11/1993 | Horrell, Jr. et al. | |
| 2011/0160470 A1 | 6/2011 | Henstock et al. | |
| 2015/0080590 A1 | 3/2015 | Jovanovic et al. | |

FOREIGN PATENT DOCUMENTS

| | | |
|---|---|---|
| EP | 2644604 | 2/2013 |
| JP | S62-103072 | 5/1987 |
| JP | H6-9591 | 1/1994 |
| JP | 2012-522061 | 9/2012 |
| JP | 2013-209255 | 10/2013 |
| JP | 2013209255 A | * 10/2013 |

OTHER PUBLICATIONS

Ito, M. et al, Kobe Steel Engineering Reports, 2005,vol.55 No. 2, p. 105-108.
International Preliminary Report on Patentability, PCT/JP2015/060265, dated Oct. 13, 2016.
Supplementary European Search Report, EP15774332, dated Sep. 29, 2017.
Official Action for Decision of Refusal dated Jan. 23, 2018.
Official Notice of Reason for Refusal dated Oct. 17, 2017, JP2014-074438.

* cited by examiner

*Primary Examiner* — Noble E Jarrell
*Assistant Examiner* — John S Kenyon
(74) *Attorney, Agent, or Firm* — Porzio Bromberg & Newman P.C.

(57) ABSTRACT

To provide a novel technique capable of further reducing the argon purge amount in a process for producing ethylene oxide.
A method for producing ethylene oxide, including: a step of supplying an ethylene oxide-containing reaction product gas produced in an ethylene oxidation reaction step in an ethylene oxidation reactor, in which ethylene is subjected to contact gas-phase oxidation using a molecular oxygen-containing gas in the presence of a silver catalyst, to an ethylene oxide absorption column to bring the reaction product gas into contact with an absorption liquid supplied to the ethylene oxide absorption column, supplying an ethylene oxide-containing column bottom liquid of the ethylene oxide absorption column to an ethylene oxide purification system, and purifying ethylene oxide in the ethylene oxide purification system; and a step of supplying at least part of a carbon dioxide gas-containing gas discharged from a column top part of the ethylene oxide absorption column to a carbon dioxide gas absorption column to bring the carbon dioxide gas-containing gas into contact with an absorption liquid, extracting the resulting carbon dioxide gas-rich absorption liquid as a column bottom liquid of the carbon dioxide gas absorption column and supplying the same to an upper part of a carbon dioxide gas stripper column, and stripping a carbon dioxide gas from the carbon dioxide gas-rich absorption liquid and discharging the same from a column top part of the carbon dioxide gas stripper column as an exhaust gas, the concentration of molecular oxygen ($O_2$) in the molecular oxygen-containing gas supplied from outside the system into the system being 99.7% by volume or more.

5 Claims, 3 Drawing Sheets

PROCESS FOR PRODUCING ETHYLENE OXIDE

TECHNICAL FIELD

The present invention relates to a method for producing ethylene oxide.

BACKGROUND ART

Nowadays, ethylene oxide is produced by catalytic gas phase oxidation of ethylene using a molecular oxygen-containing gas in the presence of a silver catalyst. An outline of a purifying method in a process for producing ethylene oxide is as follows (for example, refer to JP 62-103072 A).

First, ethylene and a molecular oxygen-containing gas are subjected to catalytic gas phase oxidation on a silver catalyst to obtain an ethylene oxide-containing reaction product gas (reaction step). Subsequently, the resulting reaction product gas is introduced into an ethylene oxide absorption column. The reaction product gas is brought into contact with an absorption liquid mainly containing water. Ethylene oxide is recovered as an aqueous solution (absorption step). Subsequently, the recovered ethylene oxide aqueous solution is fed to a purification system of ethylene oxide to obtain high-purity ethylene oxide through several stages. The ethylene oxide purification system usually includes a stripping step, a dehydration step, a light fraction separation step, a heavy fraction separation (purification) step, and the like.

Usually, an exhaust gas discharged from a column top part of the ethylene oxide absorption column, which contains unreacted ethylene, carbon dioxide and water as by-products, and an inert gas (nitrogen, argon, methane, ethane, or the like) is circulated into an ethylene oxidation step as it is. Alternatively, a part thereof is extracted and introduced into a carbon dioxide absorption column, the carbon dioxide is selectively absorbed by an alkali absorption liquid and the carbon dioxide is stripped and recovered from the absorption liquid.

Meanwhile, the molecular oxygen-containing gas, which is a reaction raw material, contains argon. As described above, when the exhaust gas from a column top part of the ethylene oxide absorption column is simply circulated in the ethylene oxidation step or the carbon dioxide absorption step, argon is accumulated in the process circulating gas. When argon is accumulated in the process circulating gas, the pressure of the reaction system may increase, making operation at constant pressure impossible. In addition, when the concentration of argon in the process circulating gas becomes too high, due to decreases in the ethylene concentration and the oxygen concentration, the EO reaction rate may decrease. Thus, usually, the exhaust gas from the column top part of the ethylene oxide absorption column is partially extracted and purged (argon purging).

As described above, the exhaust gas from the column top part of the absorption column (absorption column exhaust gas) to be purged with argon contains ethylene, which is a raw material for the production of ethylene oxide, and the amount of ethylene loss caused by argon purging is as much as 0.55% of the amount of ethylene fed to the ethylene oxidation reactor. Therefore, it has been demanded to reduce the argon purge amount.

SUMMARY OF INVENTION

The present invention has been accomplished in light of the former situation described above, and an object thereof is to provide a novel technique capable of further reducing the argon purge amount in a process for producing ethylene oxide.

The present inventors have conducted extensive research in light of the problems described above. In the course of research, they have ascertained that a trace amount of nitrogen or argon contained in a molecular oxygen-containing gas, which is supplied from outside the system into the system for use in the contact gas-phase oxidation reaction in an ethylene oxidation reactor, is incorporated into the process, and this has been a cause of an increase in the argon purge amount.

They have further found that, when the concentration of molecular oxygen ($O_2$) in the above molecular oxygen-containing gas is made equal to or more than a predetermined value, the incorporation of nitrogen or argon from the molecular oxygen-containing gas into the process can be suppressed, thereby making it possible to reduce the argon purge amount; they have thus accomplished the present invention.

That is, an aspect of the present invention relates to a method for producing ethylene oxide. This production method includes, first, a step of supplying an ethylene oxide-containing reaction product gas produced in an ethylene oxidation reaction step in an ethylene oxidation reactor, in which ethylene is subjected to contact gas-phase oxidation using a molecular oxygen-containing gas in the presence of a silver catalyst, to an ethylene oxide absorption column to bring the reaction product gas into contact with an absorption liquid supplied to the ethylene oxide absorption column, supplying an ethylene oxide-containing column bottom liquid of the ethylene oxide absorption column to an ethylene oxide purification system, and purifying ethylene oxide in the ethylene oxide purification system. In addition, this production method includes a step of supplying at least part of a carbon dioxide gas-containing gas discharged from a column top part of the ethylene oxide absorption column to a carbon dioxide gas absorption column to bring the carbon dioxide gas-containing gas into contact with an absorption liquid, extracting the resulting carbon dioxide gas-rich absorption liquid as a column bottom liquid of the carbon dioxide gas absorption column and supplying the same to an upper part of a carbon dioxide gas stripper column, and stripping a carbon dioxide gas from the carbon dioxide gas-rich absorption liquid and discharging the same from a column top part of the carbon dioxide gas stripper column as an exhaust gas.

Further, the method for producing ethylene oxide according to this aspect is characterized in that the concentration of molecular oxygen ($O_2$) in the molecular oxygen-containing gas supplied from outside the system into the system is 99.7% by volume or more.

DESCRIPTION OF EMBODIMENTS

According to an aspect of the present invention, provided is a method for producing ethylene oxide, including:

a step of supplying an ethylene oxide-containing reaction product gas produced in an ethylene oxidation reaction step in an ethylene oxidation reactor, in which ethylene is subjected to contact gas-phase oxidation using a molecular oxygen-containing gas in the presence of a silver catalyst, to an ethylene oxide absorption column to bring the reaction product gas into contact with an absorption liquid supplied to the ethylene oxide absorption column, supplying an ethylene oxide-containing column bottom liquid of the ethylene oxide absorption column to an ethylene oxide purification system, and purifying ethylene oxide in the ethylene oxide purification system; and a step of supplying at least part of a carbon dioxide gas-containing gas discharged from a column top part of the ethylene oxide absorption column to a carbon dioxide gas absorption column to bring the carbon dioxide gas-containing gas into contact with an absorption liquid, extracting the resulting carbon dioxide gas-rich absorption liquid as a column bottom liquid of the carbon dioxide gas absorption column and supplying the same to an upper part of a carbon dioxide gas stripper column, and stripping a carbon dioxide gas from the carbon dioxide gas-rich absorption liquid and discharging the same from a column top part of the carbon dioxide gas stripper column as an exhaust gas, the concentration of molecular oxygen ($O_2$) in the molecular oxygen-containing gas supplied from outside the system into the system being 99.7% by volume or more.

According to such a method for producing ethylene oxide of the present invention, in a process for producing ethylene oxide, the concentration of molecular oxygen ($O_2$) in a molecular oxygen-containing gas supplied from outside the system into the system is made 99.7% by volume or more, whereby the incorporation of nitrogen or argon derived from the molecular oxygen-containing gas into the process is suppressed. As a result, the argon purge amount in the process for producing ethylene oxide can be reduced.

Figure 1:
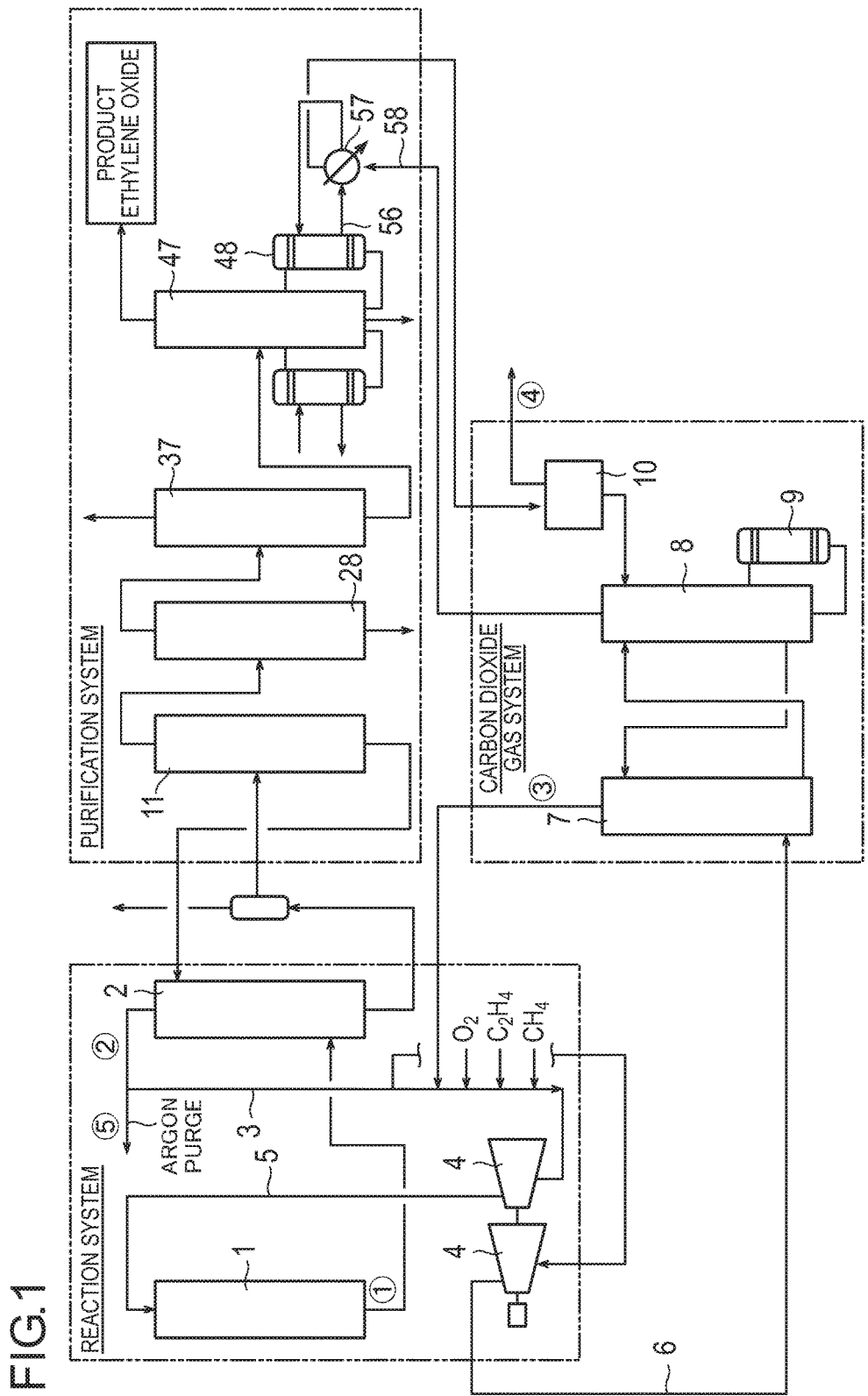
FIG. 1 is a block diagram illustrating an example of the configuration of a process for implementing a method for producing ethylene oxide according to one embodiment of the present invention.
Figure 2:
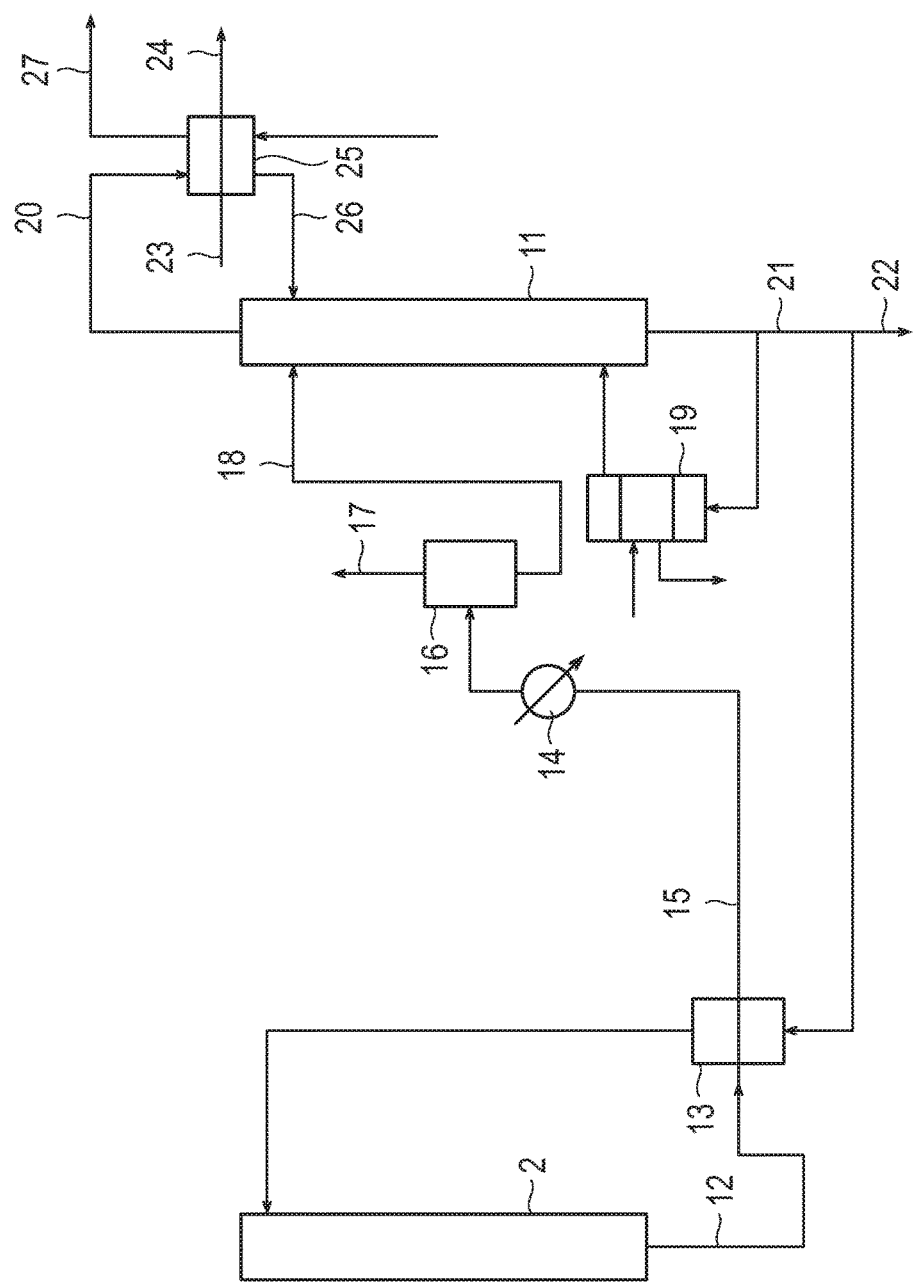
FIG. 2 is a block diagram illustrating an example of the configuration of a process for implementing a method for producing ethylene oxide according to one embodiment of the present invention.
Figure 3:
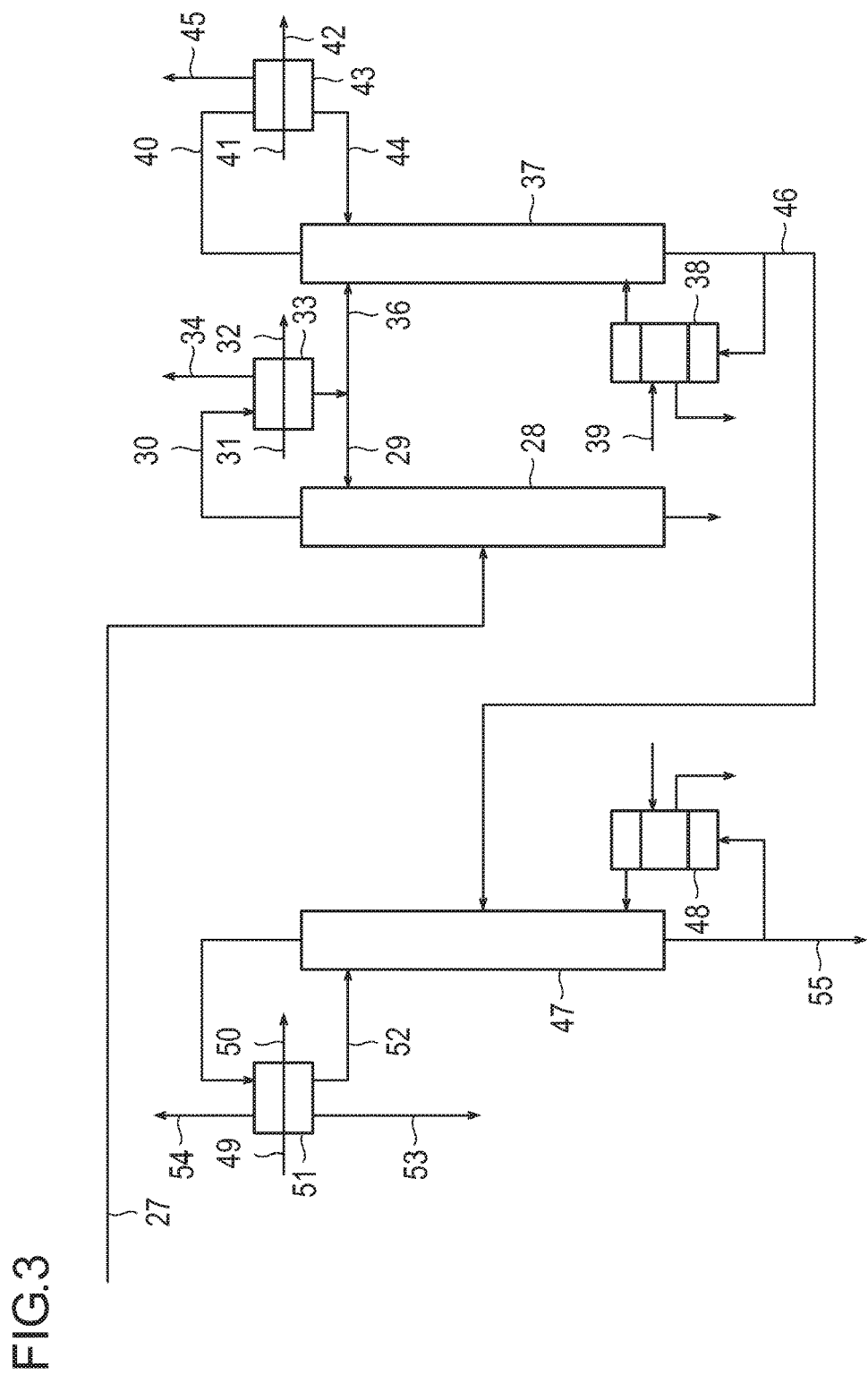
FIG. 3 is a block diagram illustrating an example of the configuration of a purification step until when the stripped ethylene oxide is eventually purified.

Hereinafter, specific embodiments for carrying out the present invention will be described in detail with reference to the drawings. However, the technical scope of the present invention should be determined based on the description of claims, and is not limited only to the following embodiments. Incidentally, in FIG. 1 to FIG. 3, 1 is an ethylene oxidation reactor, 2 is an ethylene oxide absorption column, 4 is a pressurizing blower, 7 is a carbon dioxide gas absorption column, 8 is a carbon dioxide gas stripper column, 9 is a reboiler, 10 is a gas-liquid contact part, 11 is an ethylene oxide stripper column, 13 is an heat exchanger, 14 is a reboiler, 16 is a gas-liquid separation tank, 19 is a stripper column reboiler, 25 is a stripper column condenser, 28 is a dehydrating column, 33 is a dehydrating column condenser, 37 is a light fraction separation column, 38 is a light fraction separation column reboiler, 43 is a light fraction separation column condenser, 47 is an ethylene oxide purification column, 48 is a purification column reboiler, 51 is a purification column condenser, 56 is a circulation path, 57 is a heat exchanger, and 58 is a conduit.

<<Reaction System>>

First, a system of producing ethylene oxide by an oxidation reaction of ethylene (hereinafter, also simply referred to as "reaction system") will be described with reference to FIG. 1. FIG. 1 is a block diagram illustrating a constructive example of a process in which a method for producing ethylene oxide according to an embodiment of the present invention is carried out. The process for producing ethylene oxide illustrated in FIG. 1 is roughly divided into three systems of a reaction system, a carbon dioxide gas system, and a purification system.

"An ethylene oxide-containing reaction product gas" used in the present invention is only required to be produced by a step in which ethylene is subjected to catalytic gas phase oxidation using a molecular oxygen-containing gas in the presence of a silver catalyst (hereinafter, also referred to as "ethylene oxidation reaction step"). The technology itself of the catalytic gas phase oxidation reaction is popular, and conventionally known knowledge thereof can be appropriately referred to in order to carry out the present invention. Specific embodiments such as a composition of the reaction product gas are not particularly limited. As an example, the reaction product gas usually contains, in addition to ethylene oxide in an amount of 0.5 to 5% by volume, unreacted oxygen, unreacted ethylene, generated water, a gas such as carbon dioxide, nitrogen, argon, methane, or ethane, an aldehyde such as formaldehyde or acetaldehyde, and a small amount of an organic acid such as acetic acid.

When FIG. 1 is referred to, first, a raw material gas containing ethylene or molecular oxygen is pressurized by a pressurizing blower 4, and then is heated by a heat exchanger (not illustrated) to be supplied to an ethylene oxidation reactor 1. The ethylene oxidation reactor 1 is usually a multi-tubular reactor provided with many reaction tubes filled with a silver catalyst. The reaction product gas produced in the ethylene oxidation reaction step is cooled by passing through a heat exchanger (not illustrated). Thereafter, the reaction product gas is supplied to an ethylene oxide absorption column (hereinafter, also simply referred to as "absorption column") 2. Specifically, the reaction product gas is supplied from a column bottom part of the absorption column 2. Meanwhile, an absorption liquid mainly containing water is supplied from a column top part of the absorption column 2. Counter flow contact between a gas and a liquid is thereby conducted in the absorption column 2. Ethylene oxide (usually, 99% by weight or more) included in the reaction product gas is absorbed in the absorption liquid. In addition to ethylene oxide, ethylene, oxygen, carbon dioxide, an inert gas (nitrogen, argon, methane, ethane, or the like), a low boiling point impurity such as formaldehyde, and a high boiling point impurity such as acetaldehyde or acetic acid, which are produced in the ethylene oxidation reaction step, are absorbed at the same time in substantial amounts thereof. The temperature of the reaction product gas supplied to the absorption column 2 is preferably about 20 to 80° C. A composition of the absorption liquid is not particularly limited. In addition to a liquid mainly containing water, such propylene carbonate as disclosed in JP 8-127573 A may be used as an absorption liquid. An additive can be added to the absorption liquid as necessary. Examples of the additive which can be added to the absorption liquid include a defoaming agent and a pH adjusting agent. As the defoaming agent, any defoaming agent which is insert to ethylene oxide, ethylene glycol as a by-product, or the like, and has a defoaming effect of the absorption liquid can be used. However, a typical example thereof is a water-soluble silicone emulsion because the water-soluble silicone emulsion is effective due to excellent dispersibility in the absorption liquid, excellent dilution stability, and excellent thermal stability. Examples of the pH adjusting agent include a compound which can be dissolved in the absorption liquid, such as a hydroxide or a carbonate of an alkali metal such as potassium or sodium. Preferable examples thereof include potassium hydroxide and sodium hydroxide. The pH of the absorption liquid is preferably 5 to 12, more preferably 6 to 11.

As the absorption column 2, a plate column type or packed column type absorption column can be usually used. As an operation condition of the absorption column 2, a concentration of ethylene oxide in the reaction product gas is 0.5 to 5% by volume, preferably 1.0 to 4% by volume, and an operation pressure of the absorption column 2 is 0.2 to 4.0 MPa gauge, preferably 1.0 to 3.0 MPa gauge. An absorption operation is more advantageous as the pressure is higher. However, a possible value thereof can be determined according to an operation pressure of the oxidation reactor. A molar ratio of flow rate (L/V) of the absorption liquid with respect to the reaction product gas is usually 0.30 to 2.00. A space linear velocity (GHSV[NTP]) of the reaction product gas under the standard state is usually 400 to 6000 $h^{-1}$.

A gas not absorbed in the absorption column 2, containing ethylene, oxygen, carbon dioxide, an inert gas (nitrogen, argon, methane, or ethane), aldehyde, an acid substance, or the like, is discharged from the column top part of the absorption column 2 through a conduit 3. The exhaust gas is pressurized by the pressurizing blower 4, and then is circulated into the ethylene oxidation reactor 1 through a conduit 5. Details of the ethylene oxidation reaction step are as described above. Here, the ethylene oxidation reaction step is usually carried out in an oxidation reactor provided with many reaction tubes filled with a silver catalyst under pressure (pressure of about 1.0 to 3.0 MPa gauge). Therefore, it is necessary to pressurize the exhaust gas from the column top part of the absorption column 2 using a pressurizing unit such as the pressurizing blower 4 before the exhaust gas is circulated into the ethylene oxidation reaction step.

The present invention is characterized in that the concentration of molecular oxygen ($O_2$) in the molecular oxygen-containing gas supplied from outside the system into the system is 99.7% by volume or more. Here, the "molecular oxygen-containing gas supplied from outside the system into the system" means a molecular oxygen-containing gas (shown as "$O_2$" in FIG. 1) supplied to the conduit 3 that connects the column top part of the absorption column 2 and the pressurizing blower 4.

As described above, in the course of an attempt to reduce the argon purge amount in a process for producing ethylene oxide, the present inventors have ascertained that a trace amount of nitrogen or argon contained in a molecular oxygen-containing gas, which is supplied from outside the system into the system for use in the contact gas-phase oxidation reaction in an ethylene oxidation reactor, is incorporated into the process, and this has been a cause of an increase in the argon purge amount. They have further found that, when the concentration of molecular oxygen ($O_2$) in the above molecular oxygen-containing gas is made equal to or more than a predetermined value, the incorporation of nitrogen or argon from the molecular oxygen-containing gas into the process can be suppressed, thereby making it possible to reduce the argon purge amount; they have thus accomplished the present invention.

Incidentally, in the present invention, it is necessary that the concentration of molecular oxygen ($O_2$) in the molecular oxygen-containing gas supplied into the system is 99.7% by volume or more. However, the specific technique for obtaining such a molecular oxygen-containing gas having a high $O_2$ concentration is not particularly limited. For example, techniques such as cryogenic separation and PSA can be employed to obtain a high-concentration molecular oxygen-containing gas as described above.

In addition, the present inventors have also conducted research about the reduction of the argon purge amount from different points of view from the above. As a result, they have ascertained that the incorporation of nitrogen into the process from a shaft sealing device (so-called shaft sealing) of a pressurizing blower for pressurizing the raw material gas supplied to an ethylene oxidation reactor has also been a cause of an increase in the argon purge amount. Further, they have found that also, when a centrifugal compressor in which the sealing style of the shaft sealing device is dry gas sealing is employed as the pressurizing blower, the incorporation of nitrogen into the process from the pressurizing blower can be suppressed.

According to the dry gas sealing, at a narrow sealed part having a vertical end, a gas pressure is generated by rotation, and, with a gas membrane in a non-contact manner (the gap is a few microns), the sealing function is exerted while generating minimum gas leakage. Incidentally, a centrifugal compressor equipped with a dry gas sealing as a shaft sealing device itself belongs to the known art, and there are a large number of literatures related thereto.

Here, according to the research by the present inventors based on the above findings, theoretically, it is expected that, when a molecular oxygen-containing gas having a molecular oxygen ($O_2$) concentration of 99.7% by volume or more is used, and also the above predetermined centrifugal compressor is used as a pressurizing blower, argon purging will be unnecessary. Therefore, they have performed a process for producing ethylene oxide combining the above two techniques, without argon purging. As a result, surprisingly, it has been observed that the amount of nitrogen in the process, which was expected to be discharged outside the system only by argon purging, significantly decreases over time. When the amount of nitrogen in the process significantly decreases over time like this, the mass balance of the raw material gas supplied to the ethylene oxidation reactor is disturbed, causing another specific problem in that the operation pressure in the reaction system decreases. Thus, they have found that, when a process for producing ethylene oxide is performed combining the above two techniques without argon purging, it is preferable that the process is performed while supplying an inert gas (nitrogen, argon, etc., (preferably nitrogen)) into the system together with the molecular oxygen-containing gas (see Example 2).

<<Carbon Dioxide Gas System>>

As illustrated in FIG. 1, at least a part of the gas (carbon dioxide-containing gas) discharged from the column top part of the absorption column 2 is pressurized by a pressurizing unit such as the pressurizing blower 4 to be supplied to a carbon dioxide gas absorption column 7 through a conduit 6. Hereinafter, a carbon dioxide gas recovery system (hereinafter, also simply referred to as "carbon dioxide gas system") starting from introduction of a gas into the carbon dioxide gas absorption column 7 will be described with reference to FIG. 1.

As described above, when the gas discharged from the column top part of the absorption column 2 is pressurized and introduced into the carbon dioxide gas absorption column 7 (through a conduit 6), the gas pressure at that time is adjusted to about 0.5 to 4.0 MPa gauge, and the gas temperature is adjusted to about 80 to 120° C. A carbon dioxide gas stripper column 8 is disposed in a post-stage of the carbon dioxide gas absorption column 7. An alkali absorption liquid is supplied from a column bottom part of the carbon dioxide gas stripper column 8 to an upper part of the carbon dioxide gas absorption column 7. A carbon dioxide gas and a small amount of inert gas (for example, ethylene, methane, ethane, oxygen, nitrogen, argon), contained in the gas introduced into the carbon dioxide gas absorption column 7, are absorbed by counter flow contact with the alkali absorption liquid. An unabsorbed gas discharged from the column top part of the carbon dioxide gas absorption column 7 is circulated into the conduit 3, is mixed with oxygen, ethylene, methane, or the like newly replenished, and then is circulated into the ethylene oxidation reactor 1.

The carbon dioxide gas-rich absorption liquid which has absorbed the carbon dioxide gas in the carbon dioxide gas absorption column 7 is extracted from the column bottom part of the carbon dioxide gas absorption column. Thereafter, the pressure thereof is adjusted to 0.01 to 0.5 MPa gauge, and the temperature thereof is adjusted to about 80 to 120° C. The carbon dioxide gas-rich absorption liquid is supplied to an upper part of the carbon dioxide gas stripper column 8 provided with a reboiler 9 at the column bottom part thereof. The absorption liquid causes pressure flash due to a pressure difference between the carbon dioxide gas absorption column 7 and the carbon dioxide gas stripper column 8 in a liquid feeding part in the upper part of the carbon dioxide gas stripper column 8. Because of the pressure flash, 10 to 80% by volume of carbon dioxide gas and most inert gases in the absorption liquid are separated from the absorption liquid, and discharged as an exhaust gas from the column top part of the carbon dioxide gas stripper column 8. In this embodiment, as shown in FIG. 1, it is preferable that the exhaust heat of the exhaust gas is used as a heat source in the ethylene oxide purification column in the purification system (the details will be described below). Here, in terms of reducing the amount of steam fed to the reboiler 9 of the carbon dioxide gas stripper column 8, the operation pressure of the carbon dioxide gas stripper column 8 is the smaller the better. Specifically, the operation pressure of the carbon dioxide gas stripper column 8 is preferably 0 to 0.1 MPa gauge, and more preferably 0.01 to 0.015 MPa gauge.

The remaining carbon dioxide gas absorption liquid after a part of the carbon dioxide gas is separated because of the above-described pressure flash enters a gas-liquid contact part 10 provided below the liquid feeding part. The carbon dioxide gas absorption liquid is subjected to counter flow contact with a gas mainly containing steam produced in the reboiler 9 and a carbon dioxide gas produced in the gas-liquid contact part 10 or in parts below the gas-liquid contact part 10. Apart of the carbon dioxide gas in the absorption liquid and most of the other inert gases are separated from the absorption liquid. By a series of the processes in the carbon dioxide gas system, a high-purity carbon dioxide gas is obtained from a part ranging from the top to the lower part of the gas-liquid contact part 10, preferably from the inside of the carbon dioxide gas stripper column 8 below the gas-liquid contact part 10 corresponding to one or more number of theoretical stages, necessary for gas-liquid contact. That is, in the gas-liquid contact part 10, the inert gas in the carbon dioxide gas absorption liquid is subjected to counter flow gas-liquid contact by water vapor and a carbon dioxide gas containing an extremely small amount of inert gas which comes up from the lower part, and is stripped. This makes the concentration of the inert gas extremely low. Therefore, if the gas after being stripped is extracted, a high-purity carbon dioxide gas is obtained.

<<Purification System>>

The absorption liquid which has absorbed ethylene oxide in the absorption column 2 is fed to an ethylene oxide purification system (hereinafter, also simply referred to as "purification system") as a column bottom liquid of the absorption column 2. Specific embodiments of the purification system are not particularly limited. Conventionally known knowledge thereof can be appropriately referred to. The purification system usually includes a stripping step, a dehydration step, a light fraction separation step, a heavy fraction separation (purification) step, and the like. Hereinafter, a purification system including some of these steps will be described with reference to FIGS. 2 and 3. FIG. 2 is a block diagram illustrating a constructive example of a process for performing the process for producing ethylene oxide according to the embodiment of the present invention.

The column bottom liquid (absorption liquid) of the absorption column 2 is usually heated to a temperature suitable for stripping in an ethylene oxide stripper column (hereinafter, also simply referred to as "stripper column") 11 in advance before being supplied to the stripper column 11. Specifically, as illustrated in FIG. 2, the column bottom liquid (absorption liquid) of the absorption column 2 is supplied to a heat exchanger 13 through a conduit 12. In the heat exchanger 13, heat exchange with the column bottom liquid of the stripper column 11 is performed. Furthermore, if necessary, the column bottom liquid (absorption liquid) of the absorption column 2 is heated by a heater 14 to a temperature of about 70 to 110° C. In the present embodiment, the column bottom liquid (absorption liquid) of the absorption column 2, heated by heat exchange with the column bottom liquid of the stripper column 11, is supplied to a gas-liquid separation tank 16 through a conduit 15. In the gas-liquid separation tank 16, a light fraction gas of an inert gas partially including ethylene oxide and water is separated, discharged through a conduit 17, and supplied to ethylene oxide reabsorption column (not illustrated). On the other hand, the absorption liquid as a remaining part after the light fraction gas is flashed is supplied to an upper part of the stripper column 11 through a conduit 18. In a portion where ethylene oxide and water exist together at a particularly high temperature as in the conduit 18, staying time of the absorption liquid can be short by making a disposition distance thereof as short as possible. As a result, production of ethylene glycol as a by-product can be prevented.

Subsequently, for example, as illustrate in FIG. 2, a heating medium such as water vapor is supplied to a reboiler 19, and the stripper column 11 is heated using the heating medium heated in the reboiler 19. Alternatively, the stripper column 11 is heated by directly supplying water vapor to the column bottom part of the stripper column 11. By heating the stripper column 11 in such a manner, ethylene oxide contained in the absorption liquid supplied from the upper part of the stripper column 11 (usually 99% by weight or more thereof) is stripped and discharged from the column top part of the stripper column 11 through a conduit 20. As for operation conditions of the stripper column 11, a column top pressure is usually 0.01 to 0.20 MPa gauge, and preferably 0.03 to 0.06 MPa gauge. The smaller the column top pressure is, the lower the temperature in the column is. As a result, production of ethylene glycol as a by-product from ethylene oxide in the column tends to be suppressed. However, ethylene oxide is relatively easily ignitable. Therefore, from a viewpoint of preventing leakage of oxygen into the system, usually, the operation is not performed at atmospheric pressure or lower, and is performed at a pressure a little higher than atmospheric pressure. As for temperature conditions of the stripper column 11, the column top temperature is usually 85 to 120° C., and the column bottom temperature is usually 100 to 130° C.

As illustrated in FIG. 2, the absorption liquid as a remaining part after ethylene oxide is stripped is extracted as the column bottom liquid of the stripper column 11, supplied to an upper part of the absorption column 2 as the absorption liquid of the absorption column 2, and can be circulated and used. In order to adjust the composition of the absorption liquid, fresh water or the above-described additive as necessary may be supplied to the absorption column 2 through a conduit disposed separately. The concentration of ethylene glycol in the absorption liquid supplied to the absorption column 2 is preferably maintained constant. Therefore, a part of the absorption liquid circulating between the absorption column 2 and the stripper column 11 is extracted from the column bottom part of the stripper column 11. Here, the column bottom liquid of the stripper column 11 does not contain ethylene oxide substantially. Specifically, the concentration of ethylene oxide contained in the column bottom liquid is preferably 10 ppm by weight or less, more preferably 0.5 ppm by weight or less. The column bottom liquid contains ethylene glycol produced in the absorption liquid as a by-product between the ethylene oxidation reaction step and the ethylene oxide stripping step. Apart thereof is extracted through a conduit 21 or 22. The liquid extracted through the conduit 22 is subjected to a combustion treatment or an ethylene glycol concentration step for concentrating and recovering ethylene glycol contained therein. Furthermore, in some cases, it is possible to recover ethylene glycol contained in the extracted liquid as a fiber grade product by performing a chemical treatment and, in some cases, a physical treatment to the ethylene glycol as it is or the ethylene glycol after being subjected to the ethylene glycol concentration step. The chemical treatment is, for example, disclosed in JP 45-9926 B or JP 04-28247 B. The column bottom liquid of the stripper column 11 also contains a low boiling point impurity such as formaldehyde and a high boiling point impurity such as acetaldehyde or acetic acid. Therefore, as described above, accumulation of these impurities in the absorption liquid circulated into the absorption column 2 can be advantageously prevented by extracting a part thereof to the outside of the system. On the other hand, the column bottom liquid of the stripper column which was not extracted through the conduit 22 is circulated to the column top part of the absorption column 2 after being cooled due to heat exchange with the column bottom liquid of the absorption column 2 by running through the heat exchanger 13.

The ethylene oxide-containing stripped substance stripped from the column top part of the stripper column 11 is fed through the conduit 20 to a stripper column condenser 25 in which cooling water passes through conduits 23 and 24. The condensed liquid is refluxed to the column top part of the stripper column 11 through a conduit 26. Uncondensed steam is supplied to a dehydrating column 28 (FIG. 3) through a conduit 27.

The ethylene oxide-containing steam supplied to the dehydrating column 28 comes into contact with a liquid to be refluxed through a conduit 29, and becomes steam having a higher concentration of ethylene oxide. A liquid extracted from the column bottom and having a low concentration of ethylene oxide is fed to the stripper column condenser 25 through a conduit.

The ethylene oxide-containing steam discharged from the column top part of the dehydrating column 28 is fed through a conduit 30 to a dehydrating column condenser 33 in which cooling water passes through conduits 31 and 32. A part of the condensed liquid is refluxed to the column top part of the dehydrating column 28 through the conduit 29. Uncondensed steam (ethylene oxide-containing uncondensed gas) of the dehydrating column condenser 33 is supplied to an ethylene oxide reabsorption column (not illustrated) through a conduit 34. Similarly to the absorption column 2, in the ethylene oxide reabsorption column, ethylene oxide is reabsorbed upon counter-flow contact with the absorption liquid. Here, the composition and pH of the absorption liquid used for the reabsorption of ethylene oxide in the reabsorption column, the form of the reabsorption column (plate column type or packed column type), the operation conditions, and the like are the same as those described above for the absorption column 2. Incidentally, similarly to the column bottom liquid of the absorption column 2, the column bottom liquid of the ethylene oxide reabsorption column is circulated to the purification system (in this embodiment, specifically, the stripper column 11). Meanwhile, the uncondensed gas that has not been absorbed in the ethylene oxide reabsorption column is discharged from the column top part. The uncondensed gas discharged from the ethylene oxide reabsorption column is, after the pressure is increased by a pressurizing means, circulated to the absorption column 2 or the carbon dioxide gas absorption column 7 (in the embodiment shown in FIG. 1, although not illustrated, the gas is circulated to the absorption column 2). However, it is preferable that the uncondensed gas is circulated to the carbon dioxide gas absorption column 7. This uncondensed gas contains a large amount of carbon dioxide gas (usually about 5 to 60% by volume). Accordingly, when configured as above, the concentration of carbon dioxide gas in the gas supplied from the absorption column 2 to the carbon dioxide gas absorption column 7 can be increased. As a result, the occurrence of problems caused by an increase in the amount of carbon dioxide gas in the gas supplied to the carbon dioxide gas absorption column 7 is prevented, whereby the carbon dioxide gas can be more efficiently recovered from the process for producing ethylene oxide. More specifically, at least one of the following effects, which are industrially extremely advantageous, can be obtained: reduction of the amount of steam fed to the reboiler 9 of the carbon dioxide gas stripper column 8, reduction of the feed amount of carbon dioxide gas absorption promoter, reduction of the pressurizing blower power resulting from the reduction of the gas flow fed from the absorption column 2 to the carbon dioxide gas absorption column 7, downsizing of the facilities of the carbon dioxide gas absorption column 7, improvement in the yield of ethylene oxide resulting from the reduction of the concentration of carbon dioxide gas at the inlet of the ethylene oxidation reactor 1.

The remaining part of the condensed liquid of the dehydrating column condenser 33 is supplied to a light fraction separation column 37 through a conduit 36. After heating by a method in which heating is performed using a reboiler 38 of the light fraction separation column 37 with a heating media (such as water vapor) through a conduit 39, ethylene oxide steam containing a light fraction is fed from the column top part of the light fraction separation column 37 through a conduit 40 to alight fraction separation column condenser 43 in which cooling water passes through conduits 41 and 42. The condensed liquid is refluxed to the column top part of the light fraction separation column 37 through a conduit 44, and the uncondensed steam (ethylene oxide-containing uncondensed gas) of the light fraction separation column condenser 43 is supplied through a conduit 45 to the above ethylene oxide reabsorption column to recover ethylene oxide.

The column bottom liquid of the light fraction separation column 37 is supplied to an ethylene oxide purification column (hereinafter, also simply referred to as "purification column") 47 through a conduit 46. The purification column 47 is provided with a reboiler 48 at its column bottom part. Further, in this embodiment, water vapor having a pressure of about 0.05 to 0.10 MPa gauge is supplied to the reboiler 48 of the purification column 47 as a heating medium for heating the reboiler 48. However, the heating media may alternatively be an aqueous glycol solution, warm water, or the like, for example.

As described above, it is preferable that the heating medium for heating the reboiler 48 of the purification column 47 is heated by heat exchange with exhaust gas from the column top part of the carbon dioxide gas stripper column 8. In order to achieve this, a heat exchanger 57 is installed on a circulation path 56 for the above heating medium (water vapor) to the reboiler 48. Further, an exhaust gas from the column top part of the carbon dioxide gas stripper column 8 is supplied to the heat exchanger 57 through a conduit 58. As a result, heat is exchanged with the heating media (water vapor), whereby the heating medium (water vapor) is heated. Incidentally, the exhaust gas after heat exchange in the heat exchanger 57 may be circulated in a gas-liquid separation part 10 of the carbon dioxide gas stripper column 8 as shown in FIG. 1, and then purged into the atmosphere.

Here, for safety reasons, it is undesirable to operate the purification column 47 at a high temperature. Accordingly, the purification column 47 is characterized in that its temperature is lower than the operation temperatures of other distillation columns. The column top temperature of the carbon dioxide gas stripper column 8 is as relatively low as 87° C. An exhaust gas of this temperature can be used as a heat source of the purification column 47. That is, the exhaust gas from the column top part of the carbon dioxide gas stripper column 8 is steam containing a carbon dioxide gas, and, in order to enhance the heat recovery efficiency of the steam in the exhaust gas, the difference in temperature of between the subjects to be heat-exchanged is the greater the better. Accordingly, the temperature of the subject with which the exhaust gas is heat-exchanged is the lower the better.

When the heating medium is supplied to the reboiler 48 as described above, purification is performed at a column bottom temperature of the purification column 47 of 35 to 80° C. at a column bottom pressure of the purification column 47 of 0.10 to 0.80 MPa gauge, and ethylene oxide steam having a column top temperature of 12 to 75° C. and a column top part pressure of 0.10 to 0.80 MPa gauge is fed from the column top part of the purification column 47 to a purification column condenser 51 in which cooling water passes through conduits 49 and 50. Then, ethylene oxide is liquefied in the purification column condenser 51, and apart thereof is supplied to the column top part of the purification column 47 through a conduit 52 as a reflux liquid, while the remaining part is extracted through a conduit 53 as a product ethylene oxide (product EO). The uncondensed steam (ethylene oxide-containing uncondensed gas) of the purification column condenser 51 is supplied through a conduit 54 to the above ethylene oxide reabsorption column to recover ethylene oxide.

Incidentally, the column bottom liquid of the purification column 47 is extracted through a conduit 55 as necessary for the separation of heavy components from high-boiling-point impurities such as acetaldehyde, water, acetic acid and the like.

As described above, the uncondensed steam discharged from the purification system (in the embodiment shown in FIG. 3, uncondensed steam from the dehydrating column condenser 33, the light fraction separation column condenser 43, and the purification column condenser 51) contains ethylene oxide. Therefore, such uncondensed steam is supplied to the above ethylene oxide reabsorption column.

EXAMPLES

Hereinafter, embodiments of the present invention will be described in further detail using examples. However, the technical scope of the present invention is not limited only to the following embodiments.

Comparative Example

Ethylene oxide was produced by the process for producing ethylene oxide illustrated in FIGS. 1 to 3. Incidentally, in this comparative example, a centrifugal compressor equipped with an oil film sealing as a shaft sealing device (two sets) was used as the pressurizing blower 4. In addition, as a molecular oxygen-containing gas supplied to the conduit 3 that connects the column top part of the absorption column 2 and the pressurizing blower 4, a gas having an $O_2$ concentration of 99.60% by volume (remainder: argon) was used. Here, the following Table 1 shows the amounts of components and operation conditions (flow rate, pressure, and temperature) at each of the positions from the circled number 1 to the circled number 5 illustrated in FIG. 1 at the time of steady operation of this comparative example.

TABLE 1

|  | (1) | (2) | (3) | (4) | (5) |
|---|---|---|---|---|---|
| Oxygen wt % | 6.0 | 9.4 | 9.8 | 0.2 | 9.4 |
| Ethylene wt % | 25.1 | 25.4 | 26.4 | 1.8 | 25.4 |
| Methane wt % | 33.6 | 34.0 | 35.3 | 1.0 | 34.0 |
| Argon wt % | 18.1 | 18.3 | 19.1 | 0.2 | 18.3 |
| Nitrogen wt % | 7.1 | 7.2 | 7.5 | 0.1 | 7.2 |
| Remainder wt % | 9.9 | 5.6 | 1.9 | 96.7 | 5.6 |
| Flow rate kg/h | 335828 | 332175 | 155476 | 3008 | 203 |
| Pressure MPaG | 2.25 | 2.25 | 2.25 | 0.015 | 2.25 |
| Temperature ° C. | 70 | 30 | 30 | 100 | 30 |

Example 1

Ethylene oxide was produced by the process for producing ethylene oxide illustrated in FIGS. 1 to 3. Incidentally, in this example, a centrifugal compressor equipped with an oil film sealing as a shaft sealing device (two sets) was used as the pressurizing blower 4. In addition, as a molecular oxygen-containing gas supplied to the conduit 3 that connects the column top part of the absorption column 2 and the pressurizing blower 4, a gas having an $O_2$ concentration of 99.95% by volume (remainder: argon) was used. Here, the following Table 2 shows the amounts of components and operation conditions (flow rate, pressure, and temperature) at each of the positions from the circled number 1 to the circled number 5 illustrated in FIG. 1 at the time of steady operation of this example.

TABLE 2

|  | (1) | (2) | (3) | (4) | (5) |
|---|---|---|---|---|---|
| Oxygen wt % | 6.3 | 9.7 | 10.1 | 0.2 | 9.7 |
| Ethylene wt % | 26.2 | 26.5 | 27.6 | 1.8 | 26.5 |
| Methane wt % | 35.0 | 35.5 | 36.9 | 1.0 | 35.5 |
| Argon wt % | 5.4 | 5.4 | 5.7 | 0.1 | 5.4 |
| Nitrogen wt % | 16.9 | 17.1 | 17.8 | 0.2 | 17.1 |
| Remainder wt % | 10.3 | 5.8 | 2.0 | 96.8 | 5.8 |
| Flow rate kg/h | 335828 | 331567 | 149074 | 3016 | 31 |
| Pressure MPaG | 2.25 | 2.25 | 2.25 | 0.015 | 2.25 |
| Temperature ° C. | 70 | 30 | 30 | 100 | 30 |

Example 2

Ethylene oxide was produced by the process for producing ethylene oxide illustrated in FIGS. 1 to 3. Incidentally, in this example, a centrifugal compressor equipped with a dry gas sealing as a shaft sealing device (two sets) was used as the pressurizing blower 4. In addition, as a molecular oxygen-containing gas supplied to the conduit 3 that connects the column top part of the absorption column 2 and the pressurizing blower 4, a gas having an $O_2$ concentration of 99.95% by volume (remainder: argon) was used. Here, the following Table 3 shows the amounts of components and operation conditions (flow rate, pressure, and temperature) at each of the positions from the circled number 1 to the circled number 5 illustrated in FIG. 1 at the time of steady operation of this example. Incidentally, argon purging is not performed in this example. Therefore, the flow rate at the circled number 5 is 0. In addition, together with the molecular oxygen-containing gas, nitrogen ($N_2$) gas was also supplied to the conduit 3 that connects the column top part of the absorption column 2 and the pressurizing blower 4 at a flow rate of 1.1 $Nm^3$/min, thereby equilibrating the mass balance.

TABLE 3

|  | (1) | (2) | (3) | (4) | (5) |
|---|---|---|---|---|---|
| Oxygen wt % | 6.3 | 9.8 | 10.2 | 0.2 |  |
| Ethylene wt % | 26.5 | 26.8 | 27.9 | 1.8 |  |
| Methane wt % | 35.4 | 35.9 | 37.4 | 1.0 |  |
| Argon wt % | 1.7 | 1.7 | 1.8 | 0.0 |  |
| Nitrogen wt % | 19.7 | 20.0 | 20.8 | 0.2 |  |
| Remainder wt % | 10.4 | 5.9 | 2.0 | 96.8 |  |
| Flow rate kg/h | 335828 | 331394 | 147316 | 3018 | 0 |
| Pressure MPaG | 2.25 | 2.25 | 2.25 | 0.015 |  |
| Temperature ° C. | 70 | 30 | 30 | 100 |  |

The amount of methane and the amount of ethylene loss during argon purging calculated from the comparative example and the Examples 1 to 2 were calculated as follows.

TABLE 4

|  |  | Example 2 High-purity $O_2$ + dry gas sealing | Example 1 High-purity $O_2$ | Comparative Example |
|---|---|---|---|---|
| (1) Argon Purge Amount | | | | |
| Argon amount in oxygen | $Nm^3$/h | 3.9 | 3.9 | 31.3 |
| Oxygen purity | vol % | 99.95 | 99.95 | 99.60 |
| Sealing gas amount $N_2$ (K-20) | $Nm^3$/h | 1.3 | 17.6 | 17.6 |
| Carbon dioxide gas system purge amount | $Nm^3$/h | 94.6 | 94.6 | 94.6 |
| $N_2$ feed amount | $Nm^3$/h | 64.5 | 0.0 | 0.0 |
| Argon purge amount | $Nm^3$/h | 0.0 | 29.9 | 188.5 |
| (2) Methane Amount, Ethylene Loss Amount | | | | |
| Methane amount | $Nm^3$/h | 0.0 | 15.2 | 95.7 |
| Reduction | $Nm^3$/h | 95.7 | 80.5 |  |
| Ethylene loss amount | $Nm^3$/h | 0.0 | 6.5 | 41.2 |
| Reduction | $Nm^3$/h | 41.2 | 34.6 |  |

From the results shown in Table 4, it can be seen that the argon purge amount can be reduced by the configuration of the present invention (by supplying a high-concentration $O_2$-containing gas into the system) (Example 1). In addition, it can be seen when a centrifugal compressor equipped with a dry gas sealing as a shaft sealing device is further used as a pressurizing blower, a process for producing ethylene oxide can be performed without performing the operation of argon purging itself (Example 2). Incidentally, at this time, it was also necessary to separately supply an inert gas, such as nitrogen, into the system together with the molecular oxygen-containing gas in order to equilibrate the mass balance.

From the above, it is understood that the present invention (further in combination with the predetermined centrifugal compressor described above) provides a method for producing ethylene oxide having extremely high economical efficiency.

This application is based on Japanese Patent Application No. 2014-074438 filed on Mar. 31, 2014, the contents of which are entirely incorporated herein by reference.

The invention claimed is:

1. A method for producing ethylene oxide, comprising: a step of supplying ethylene oxide produced in an ethylene oxidation reaction step in an ethylene oxidation reactor, in which ethylene is subjected to contact gas-phase oxidation using molecular oxygen in the presence of a silver catalyst in an ethylene oxide absorption column to bring the ethylene oxide into contact with water as an absorption liquid supplied to the ethylene oxide absorption column, supplying an ethylene oxide in column bottom liquid of the ethylene oxide absorption column to an ethylene oxide purification system, and purifying the ethylene oxide in the ethylene oxide purification system; and a step of supplying at least part carbon dioxide discharged from a column top part of the ethylene oxide absorption column to a carbon dioxide gas absorption column to bring the carbon dioxide into contact with water as an absorption liquid, extracting the resulting carbon dioxide in the absorption liquid from a column bottom of the carbon dioxide gas absorption column and supplying the resulting carbon dioxide in the absorption liquid to an upper part of a carbon dioxide gas stripper column, and stripping the carbon dioxide and discharging the carbon dioxide from a column top part of the carbon dioxide gas stripper column as an exhaust gas, the concentration of molecular oxygen (O$_2$) gas supplied from outside the system into the system being 99.7% by volume or more.

2. The method for producing ethylene oxide according to claim 1, wherein a raw material gas containing the ethylene is pressurized using a centrifugal compressor equipped with a dry gas sealing as a shaft sealing device, and the pressurized raw material gas is supplied to the ethylene oxidation reactor.

3. The method for producing ethylene oxide according to claim 2, being performed without argon purging.

4. The method for producing ethylene oxide according to claim 1, being performed while supplying nitrogen into the system together with the molecular oxygen.

5. The method for producing ethylene oxide according to claim 3, being performed while supplying nitrogen into the system together with the molecular oxygen.

\* \* \* \* \*